Figure 1:
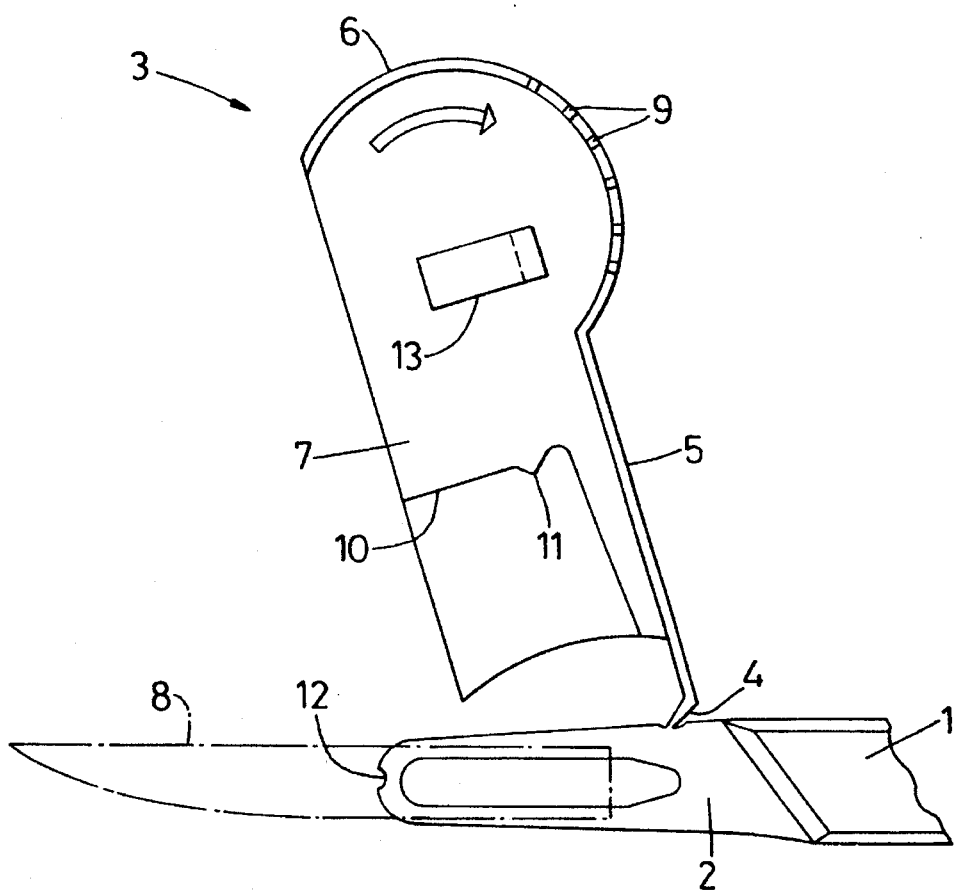

United States Patent [19]
Capewell

[11] Patent Number: 5,478,346
[45] Date of Patent: Dec. 26, 1995

[54] SCALPEL

[75] Inventor: Raymond A. Capewell, Clitheroe, United Kingdom

[73] Assignee: Granton Ragg Limited, Sheffield, England

[21] Appl. No.: 147,727

[22] Filed: Nov. 2, 1993

[30] Foreign Application Priority Data

Nov. 14, 1992 [GB] United Kingdom .................... 9223942

[51] Int. Cl.⁶ ...................................................... A61B 17/32
[52] U.S. Cl. ................... 606/167; 30/2; 30/151; 30/335
[58] Field of Search .................................. 606/166, 167; 30/2, 151, 164, 335, 339

[56] References Cited

U.S. PATENT DOCUMENTS

| | | | |
|---|---|---|---|
| 4,531,286 | 7/1985 | Vito et al. | 30/2 |
| 4,675,996 | 6/1987 | DuBuque | 30/2 |
| 4,980,977 | 1/1991 | Matin et al. | 30/2 |
| 5,330,494 | 7/1994 | van der Westhuizen et al. | 606/167 |

FOREIGN PATENT DOCUMENTS

| | | |
|---|---|---|
| 0201304 | 11/1986 | European Pat. Off. . |
| 848388 | 6/1959 | United Kingdom . |
| 2187989 | 9/1987 | United Kingdom . |

Primary Examiner—Stephen C. Pellegrino
Assistant Examiner—William W. Lewis
Attorney, Agent, or Firm—Trexler, Bushnell, Giangiorgi & Blackstone, Ltd.

[57] ABSTRACT

The invention relates to scalpels. By their nature, scalpels are exceedingly sharp, and there is the growing requirement of the provision of a guard over the blade at its point of manufacture to eliminate risk to the operative removing the scalpel from its packaging. With guards known hitherto, it is common practice to replace the guard over the blade after use. However, this introduces the risk of a used scalpel being mistaken for an unused scalpel. The objective of the invention is to avoid this possibility, an objective met by a construction comprising a handle and a blade secured to one end of the handle, and there being a blade guard attached to the scalpel by a frangible tether, the guard having a further means to engage a co-operating part of the scalpel, said further means in conjunction with said frangible tether serving to hold the guard in place over the blade.

4 Claims, 2 Drawing Sheets

SCALPEL

This invention relates to scalpels, particularly, but not necessarily exclusively, for surgical use.

Scalpels, particularly surgical scalpels, have of necessity, an exceedingly sharp cutting edge necessitating their careful handling before and after use. Known in the art is to provide packaging for scalpels of adequate strength to allow safe handling up to the point that the scalpel is required. Here there is the risk that removal of the packaging exposes the blade and it is not unknown for an operative to inadvertently cut himself at that point, harmful to the operative and rendering the scalpel unusable.

This has led to the provision of guards to surround the blade, to protect the operative during removal of the scalpel from its packaging, and hitherto the guard has been of a nature such that it can be replaced on the blade after use. Here there is the growing recognition of two potential risks, the possibility of an operative cutting himself during replacement of the guard on a dirty blade with the risk of transmittal of disease, and secondly the scalpel not being disposed of in accordance with standard procedures and subsequently being mistaken for a clean scalpel and inadvertently re-used.

Consequently, the current requirement is for the provision of a scalpel with a guard for the blade that cannot be replaced after its removal, and the object of the present invention is to provide a scalpel that meets this requirement.

According to the present invention, a scalpel comprises a handle, and a blade secured to one end of the handle, and there being a blade guard attached to the scalpel by a frangible tether, the guard having a further means to engage a co-operating part of the scalpel, said further means in conjunction with said frangible tether serving to hold the guard in place over the blade.

According to a further aspect of the present invention a scalpel comprises a handle, a blade secured at one end of the handle and a blade guard, said guard being attached to said handle by a frangible tether, and said guard having an engagement means to engage co-operating location means on the handle and whereby to maintain said guard in a position overlying said blade.

According to a still further aspect of the present invention, a scalpel comprises a handle, a blade secured to one end of the handle, and a blade guard, said blade guard being attached to the handle by a frangible tether, and said guard having a lug means to engage over the blade with a sufficient frictional contact such that the contact between the lug means and the blade combines with said frangible tether to hold the guard over the blade for so long as the tether remains intact.

Preferably, the handle and the guard are of an appropriate plastics material to enable the handle to be moulded along with the guard, with the frangible tether integral with both the handle and the guard. With the blade in place either by moulding of the handle on to the blade tang or with the blade separately applied and secured to the handle, the guard can be hinged about the tether to bring the engagement means on the guard into engagement with the co-operating means on the scalpel and when the attachment of the guard by the tether to the handle, and the engagement between the engagement means on the guard and the co-operating means on the scalpel combine to hold the guard securely about the blade.

When required to be used, the guard can simply be lifted clear of the blade, and easily detached from the handle by snapping the tether. After use, the guard, in the absence of the tethered connection to the handle, cannot be re-applied to and hold itself on the blade.

The guard means may be of generally U-shaped cross-section of a width between sidewalls marginally greater than the thickness of the blade, of a length greater than that of the blade part projecting beyond the end of the handle, and of a height greater than the width of the blade preferably however the guard is a generally plate-like member again of a length and height greater than the blade. The tether may be formed integral with the rearward edge of the end wall of the guard, and to the handle at a predetermined distance from its front end. The engagement means on the guard may be a projection formed integrally with the inner face of one sidewall of a U-shaped guard, or on the face of a plate-like guard, and at a predetermined distance from the tethered connection to the handle, and the location means on the handle may be a co-operating notch formed in the end of the handle and to the side adjacent the sidewall of the guard bearing the projection. The distance of the projection on the guard from the tethered connection to the handle is such that the projection is a snap fit with the notch at the end of the handle, and when they are engaged, a tension is applied between the projection and the tether sufficient to hold the guard in place. Alternatively, and with a generally plate-like guard, the engagement means on the guard is a generally L-shaped lug formed integrally on its face to engage over the blade part way along the length of the blade, the distance of the lug from the face of the guard being commensurate with the thickness of the blade such that there is contact between the lug and the blade to provide a friction fit sufficient, inconjunction with the tether, to hold the guard to the blade, but not sufficient to allow the guard to be replaced and held to the blade after the tether has been broken.

Preferably, the forward end of the guard is enlarged to facilitate it being gripped by the hand of the operative, and further preferably the enlarged portion has gripping formations on its outer surface.

Figure 2:
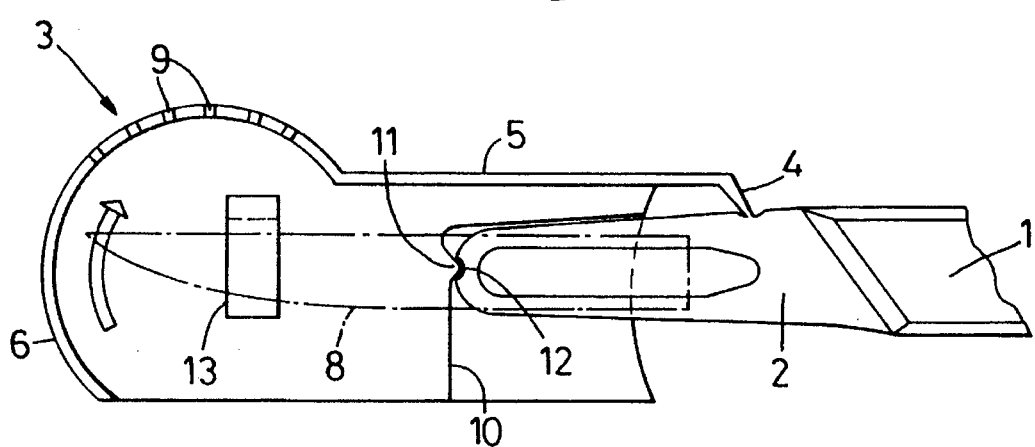
Figure 3:
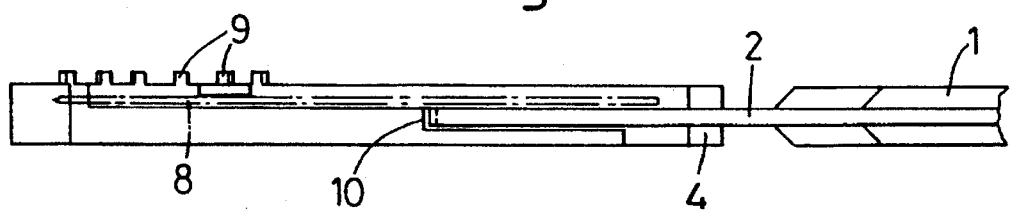

Two embodiments of the invention will now be described by way of example only, with reference to the accompanying drawings, in which:

FIG. 1 is a side elevation of a scalpel in accordance with the invention, with the scalpel guard in its position as moulded;

FIG. 2 corresponds to FIG. 1 but shows the scalpel guard in its operative position;

FIG. 3 is an underneath plan view of FIG. 2; and

Figure 4:
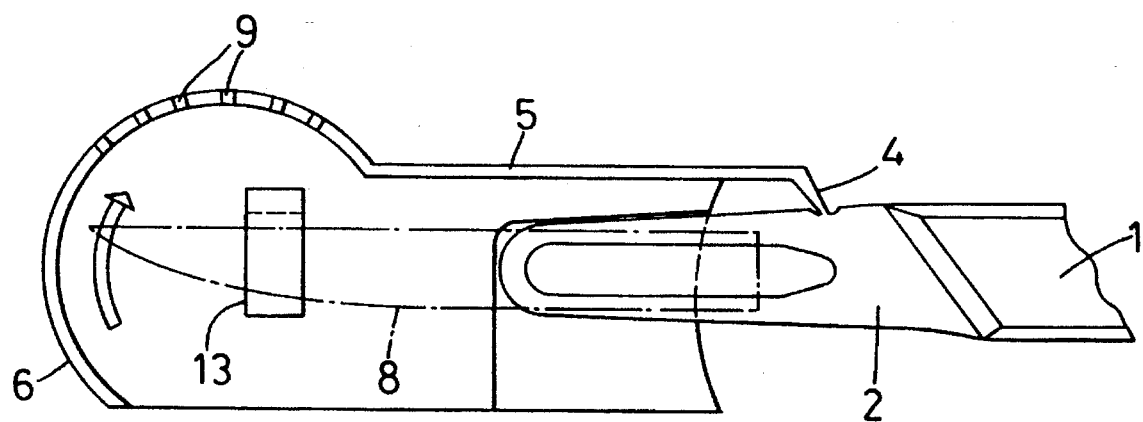

FIG. 4 corresponds to FIG. 2 but shows an alternative form of construction.

In the drawings, a scalpel has a handle 1 formed as a moulding of an appropriate plastics material, with an integral end blade locating section 2, to which a scalpel blade can be attached by its tang during the moulding of the handle or secured to the end section 2 subsequent to moulding. Also moulded along with the handle is a blade guard 3, the blade guard having an integral tether 4 attached to the end section 2 at a predetermined point along the length of the end section.

The blade guard 3 is a generally plate-like member with a peripheral flange along one side 5 and at its outer end 6, with a face 7 to lie closely adjacent the blade 8. The length of the guard is longer than that of a blade secured to the end section 2 and has a depth greather than that of the blade. Towards its outer end 6 the guard is of enlarged depth to facilitate being gripped by an operative, gripping of the guard being further enhanced by the provision of projections 9 to the side 5 of the enlarged part 6 of the guard.

On the face 7 of the guard is formed a shoulder 10 to a predetermined distance from the tether and the shoulder 10 is formed with a projection 11, the blade locating section 2 of the handle being formed during moulding with a co-operating recess 12. Following the moulding of the handle and guard with a blade, or subsequent to the securing of a blade to the end section 2, the guard is hinged about the tether 4, the predetermined location of the tether on the end section 2, and the predetermined distance of the shoulder 10 from the tether 4 being such that the projection 11 on the guard is a snap fit in the recess 12 with a sufficient tension applied between the projection and the tether to hold the guard in position over a blade.

When the scalpel is required to be used, the end part 6 is gripped and lifted to bring the projection 11 on the guard clear of the recess 12 on the end of the handle, and with the guard swung clear of the blade the tether 4 can be snapped with relative ease.

To hold the guard adjacent the blade, an integral lug 13 may be provided on the face 7 of the guard to overlie the blade when the guard is in its FIG. 2 position.

In the alternative construction depicted in FIG. 4, and where like reference numerals are employed to those employed in FIGS. 1 to 3, the lug 13 is so formed that it is spaced from the face 7 by a distance commensurate with the thickness of the blade 8. Thee situation here is that with the guard swung from its moulding position (equivalent to FIG. 1) to its operative position the lug 13 is a push fit over the blade 8 with a resultant frictional contact between the lug and the blade sufficient to provide a tension between the lug 13 and the tether 4 to hold the guard in place. When required to be used, the guard can be swung clear of the blade and the tether snapped. Following use whilst a guard can be relocated on the blade, it cannot hold itself to the blade, the frictional contact as between the lug and the blade being insufficient in the absence of the tether connection to hold the guard in place.

Consequently, with both forms of construction, following use of the scalpel, the guard cannot be relocated over the blade and hold itself in place substantially reducing any risk of a used scalpel being mistaken for an unused scalpel.

I claim:

1. A scalpel comprising a handle and a blade secured to the handle, a detachable blade guard attached to the handle by a frangible tether, the guard having a location means, and the handle having a mating location means on the end adjacent the guard to cooperate with the location means on the guard so that with the guard in place over the blade and the location and mating location means in engagement, a tension is induced in the tether sufficient to hold the guard in place over the blade, wherein a second location means on the guard is lug means to engage over the blade with a sufficient frictional contact, the contact between said lug means and said blade combining with said frangible tether to hold the guard over the blade for so long as the tether remains intact.

2. A scalpel as in claim 1, wherein the handle and the guard are of an appropriate plastics material to enable the handle to be moulded along with the guard, with the frangible tether integral with both the handle and the guard.

3. A scalpel as in claim 1, wherein the lug means is spaced from the side face by a distance commensurate with the thickness of the blade, for the lug means to be a push-fit over the blade.

4. A scalpel comprising a handle and a blade secured to one end of the handle, a detachable blade guard attached to the handle by a frangible tether, the guard being of generally U-shaped cross-section of a length and height greater than that of the blade, the U-shaped guard being closed to one side and over its outer end, and open to its opposite side and at its end of closest approach to the handle, one side wall of the guard being formed of shorter length than the other, there being a location means formed on the edge of the shorter side wall of the guard to cooperate with a mating location means on the adjacent end of the handle, the guard being attached to the handle by a frangible tether, so that with the guard in place over the blade and the location and mating location means in engagement, a tension is induced in the tether sufficient to hold the guard in place over the blade.

* * * * *